US 9,086,365 B2

(12) United States Patent
Wang et al.

(10) Patent No.: US 9,086,365 B2
(45) Date of Patent: Jul. 21, 2015

(54) QUANTIFICATION OF OPTICAL ABSORPTION COEFFICIENTS USING ACOUSTIC SPECTRA IN PHOTOACOUSTIC TOMOGRAPHY

(76) Inventors: Lihong Wang, Creve Coeur, MO (US); Zijian Guo, St. Louis, MO (US)

(*) Notice: Subject to any disclaimer, the term of this patent is extended or adjusted under 35 U.S.C. 154(b) by 144 days.

(21) Appl. No.: 13/637,897

(22) PCT Filed: Apr. 8, 2011

(86) PCT No.: PCT/US2011/031823
§ 371 (c)(1),
(2), (4) Date: Oct. 24, 2012

(87) PCT Pub. No.: WO2011/127428
PCT Pub. Date: Oct. 13, 2011

(65) Prior Publication Data
US 2013/0199299 A1 Aug. 8, 2013

Related U.S. Application Data

(60) Provisional application No. 61/322,605, filed on Apr. 9, 2010.

(51) Int. Cl.
*G01N 21/17* (2006.01)
*A61B 5/00* (2006.01)
(Continued)

(52) U.S. Cl.
CPC .......... *G01N 21/1702* (2013.01); *A61B 5/0095* (2013.01); *A61B 5/417* (2013.01); *A61B 5/7257* (2013.01); *A61B 8/13* (2013.01); *A61B 8/5215* (2013.01)

(58) Field of Classification Search
CPC ............................. A61B 5/0095; A61B 5/7257
USPC .......................... 600/310, 322, 323, 473, 476
See application file for complete search history.

(56) References Cited

U.S. PATENT DOCUMENTS 4,029,756 A   6/1977 Gaafar
4,127,318 A   11/1978 Determann et al.
(Continued)

FOREIGN PATENT DOCUMENTS

EP   0012262 A1   6/1980
EP   1 493 380 A1   1/2005
(Continued)

OTHER PUBLICATIONS

Petrov et al., "Optoacoustic, Noninvasive, Real-Time, Continuous Monitoring of Cerebral Blood Oxygenation: An In Vivo Study in Sheep", Anesthesiology, 2005, pp. 69-75, vol. 102, No. 1.
(Continued)

*Primary Examiner* — Eric Winakur
(74) *Attorney, Agent, or Firm* — Armstrong Teasdale LLP

(57) ABSTRACT

Accurately quantifying optical absorption coefficient using acoustic spectra of photoacoustic signals. Optical absorption is closely associated with many physiological parameters, such as the concentration and oxygen saturation of hemoglobin, and it can be used to quantify the concentrations of non-fluorescent molecules. A sample is illuminated by, for example, a pulsed laser and following the absorption of optical energy, a photoacoustic pressure is generated via thermoelastic expansion. The acoustic waves then propagate and are detected by a transducer. The optical absorption coefficient of the sample is quantified from spectra of the measured photoacoustic signals. Factors, such as system bandwidth and acoustic attenuation, may affect the quantification but are canceled by dividing the acoustic spectra measured at multiple optical wavelengths.

20 Claims, 10 Drawing Sheets

(51) Int. Cl.
*A61B 8/13* (2006.01)
*A61B 8/08* (2006.01)

(56) References Cited

U.S. PATENT DOCUMENTS

| | | |
|---|---|---|
| 4,255,971 A | 3/1981 | Rosencwaig |
| 4,267,732 A | 5/1981 | Quate |
| 4,375,818 A | 3/1983 | Suwaki et al. |
| 4,385,634 A | 5/1983 | Bowen |
| 4,430,897 A | 2/1984 | Quate |
| 4,462,255 A | 7/1984 | Guess et al. |
| 4,468,136 A | 8/1984 | Murphy et al. |
| 4,489,727 A | 12/1984 | Matsuo et al. |
| 4,546,771 A | 10/1985 | Eggleton et al. |
| 4,596,254 A | 6/1986 | Adrian et al. |
| 4,740,081 A | 4/1988 | Martens et al. |
| 4,802,461 A | 2/1989 | Cho |
| 4,802,487 A | 2/1989 | Martin et al. |
| 4,809,703 A | 3/1989 | Ishikawa et al. |
| 4,850,363 A | 7/1989 | Yanagawa |
| 4,860,758 A | 8/1989 | Yanagawa et al. |
| 4,869,256 A | 9/1989 | Kanno et al. |
| 4,921,333 A | 5/1990 | Brody et al. |
| 4,995,396 A | 2/1991 | Inaba et al. |
| 5,070,455 A | 12/1991 | Singer et al. |
| 5,083,549 A | 1/1992 | Cho et al. |
| 5,107,844 A | 4/1992 | Kami et al. |
| 5,115,814 A | 5/1992 | Griffith et al. |
| 5,125,410 A | 6/1992 | Misono et al. |
| 5,140,463 A | 8/1992 | Yoo et al. |
| 5,170,793 A | 12/1992 | Takano et al. |
| 5,207,672 A | 5/1993 | Roth et al. |
| 5,227,912 A | 7/1993 | Ho et al. |
| 5,305,759 A | 4/1994 | Kaneko et al. |
| 5,321,501 A | 6/1994 | Swanson et al. |
| 5,331,466 A | 7/1994 | Van Saarloos |
| 5,345,938 A | 9/1994 | Nishiki et al. |
| 5,373,845 A | 12/1994 | Gardineer et al. |
| 5,414,623 A | 5/1995 | Lu et al. |
| 5,445,155 A | 8/1995 | Sieben |
| 5,465,722 A | 11/1995 | Fort et al. |
| 5,546,947 A | 8/1996 | Yagami et al. |
| 5,546,948 A | 8/1996 | Hamm et al. |
| 5,606,975 A | 3/1997 | Liang et al. |
| 5,615,675 A | 4/1997 | O'Donnell et al. |
| 5,635,784 A | 6/1997 | Seale |
| 5,651,366 A | 7/1997 | Liang et al. |
| 5,713,356 A | 2/1998 | Kruger |
| 5,718,231 A | 2/1998 | Dewhurst et al. |
| 5,836,872 A | 11/1998 | Kenet et al. |
| 5,840,023 A | 11/1998 | Oraevsky et al. |
| 5,860,934 A | 1/1999 | Sarvazyan |
| 5,913,234 A | 6/1999 | Julliard et al. |
| 5,971,998 A | 10/1999 | Russell et al. |
| 5,991,697 A | 11/1999 | Nelson et al. |
| 6,055,097 A | 4/2000 | Lanni et al. |
| 6,102,857 A | 8/2000 | Kruger |
| 6,104,942 A | 8/2000 | Kruger |
| 6,108,576 A | 8/2000 | Alfano et al. |
| 6,111,645 A | 8/2000 | Tearney et al. |
| 6,134,003 A | 10/2000 | Tearney et al. |
| 6,216,025 B1 | 4/2001 | Kruger |
| 6,233,055 B1 | 5/2001 | Mandella et al. |
| 6,282,011 B1 | 8/2001 | Tearney et al. |
| 6,292,682 B1 | 9/2001 | Kruger |
| 6,309,352 B1 | 10/2001 | Oraevsky et al. |
| 6,341,036 B1 | 1/2002 | Tearney et al. |
| 6,379,325 B1 | 4/2002 | Benett et al. |
| 6,405,069 B1 | 6/2002 | Oraevsky et al. |
| 6,413,228 B1 | 7/2002 | Hung et al. |
| 6,421,164 B2 | 7/2002 | Tearney et al. |
| 6,432,067 B1 | 8/2002 | Martin et al. |
| 6,466,806 B1 * | 10/2002 | Geva et al. .................. 600/310 |
| 6,485,413 B1 | 11/2002 | Boppart et al. |
| 6,490,470 B1 | 12/2002 | Kruger |
| 6,498,942 B1 | 12/2002 | Esenaliev et al. |
| 6,498,945 B1 | 12/2002 | Alfheim et al. |
| 6,501,551 B1 | 12/2002 | Tearney et al. |
| 6,564,087 B1 | 5/2003 | Pitris et al. |
| 6,567,688 B1 | 5/2003 | Wang |
| 6,626,834 B2 | 9/2003 | Dunne et al. |
| 6,633,774 B2 | 10/2003 | Kruger |
| 6,654,630 B2 | 11/2003 | Zuluaga et al. |
| 6,658,279 B2 | 12/2003 | Swanson et al. |
| 6,694,173 B1 | 2/2004 | Bende et al. |
| 6,701,181 B2 | 3/2004 | Tang et al. |
| 6,751,490 B2 | 6/2004 | Esenaliev et al. |
| 6,764,450 B2 | 7/2004 | Yock |
| 6,831,781 B2 | 12/2004 | Tearney et al. |
| 6,833,540 B2 | 12/2004 | MacKenzie et al. |
| 6,839,496 B1 | 1/2005 | Mills et al. |
| 6,846,288 B2 | 1/2005 | Nagar et al. |
| 6,877,894 B2 | 4/2005 | Vona et al. |
| 6,937,886 B2 | 8/2005 | Zavislan |
| 6,956,650 B2 | 10/2005 | Boas et al. |
| 7,072,045 B2 | 7/2006 | Chen et al. |
| 7,198,778 B2 | 4/2007 | Achilefu et al. |
| 7,231,243 B2 | 6/2007 | Tearney et al. |
| 7,245,789 B2 | 7/2007 | Bates et al. |
| 7,266,407 B2 | 9/2007 | Li et al. |
| 7,322,972 B2 | 1/2008 | Viator et al. |
| 7,357,029 B2 | 4/2008 | Falk |
| 7,382,949 B2 | 6/2008 | Bouma et al. |
| 7,541,602 B2 | 6/2009 | Metzger et al. |
| 7,917,312 B2 | 3/2011 | Wang et al. |
| 8,016,419 B2 | 9/2011 | Zhang et al. |
| 8,025,406 B2 | 9/2011 | Zhang et al. |
| 8,143,605 B2 | 3/2012 | Metzger et al. |
| 8,397,573 B2 * | 3/2013 | Kobayashi ................ 73/596 |
| 8,416,421 B2 | 4/2013 | Wang et al. |
| 8,454,512 B2 | 6/2013 | Wang et al. |
| 2001/0052979 A1 | 12/2001 | Treado et al. |
| 2002/0176092 A1 | 11/2002 | Deck |
| 2003/0097066 A1 | 5/2003 | Shelby et al. |
| 2003/0160957 A1 | 8/2003 | Oldham et al. |
| 2003/0160967 A1 | 8/2003 | Houston et al. |
| 2004/0039379 A1 | 2/2004 | Viator et al. |
| 2004/0082070 A1 | 4/2004 | Jones et al. |
| 2005/0015002 A1 | 1/2005 | Dixon et al. |
| 2005/0143664 A1 | 6/2005 | Chen et al. |
| 2005/0154313 A1 | 7/2005 | Desilets et al. |
| 2005/0217381 A1 | 10/2005 | Falk |
| 2006/0055936 A1 | 3/2006 | Yun et al. |
| 2006/0058614 A1 | 3/2006 | Tsujita |
| 2006/0122516 A1 | 6/2006 | Schmidt et al. |
| 2006/0181791 A1 | 8/2006 | Van Beek et al. |
| 2006/0184042 A1 | 8/2006 | Wang et al. |
| 2006/0235299 A1 | 10/2006 | Martinelli |
| 2006/0264717 A1 | 11/2006 | Pesach et al. |
| 2007/0088206 A1 | 4/2007 | Peyman et al. |
| 2007/0213590 A1 | 9/2007 | Squicciarini |
| 2007/0213618 A1 | 9/2007 | Li et al. |
| 2007/0282200 A1 | 12/2007 | Johnson et al. |
| 2007/0299341 A1 | 12/2007 | Wang et al. |
| 2008/0088838 A1 | 4/2008 | Raicu et al. |
| 2008/0173093 A1 | 7/2008 | Wang et al. |
| 2008/0194929 A1 | 8/2008 | Pesach et al. |
| 2008/0230717 A1 | 9/2008 | Ashkenazi et al. |
| 2009/0088631 A1 | 4/2009 | Dietz et al. |
| 2009/0116518 A1 | 5/2009 | Patel et al. |
| 2009/0138215 A1 | 5/2009 | Wang et al. |
| 2010/0079768 A1 | 4/2010 | Wang et al. |
| 2010/0245766 A1 | 9/2010 | Zhang et al. |
| 2010/0245769 A1 | 9/2010 | Zhang et al. |
| 2010/0245770 A1 * | 9/2010 | Zhang et al. ................ 351/219 |
| 2010/0249562 A1 | 9/2010 | Zhang et al. |
| 2010/0268042 A1 | 10/2010 | Wang et al. |
| 2010/0285518 A1 | 11/2010 | Viator et al. |
| 2010/0309466 A1 | 12/2010 | Lucassen et al. |
| 2011/0071402 A1 | 3/2011 | Masumura |
| 2011/0122416 A1 | 5/2011 | Yang et al. |
| 2011/0201914 A1 | 8/2011 | Wang et al. |
| 2011/0275890 A1 | 11/2011 | Wang et al. |
| 2011/0282181 A1 | 11/2011 | Wang et al. |

(56) References Cited

U.S. PATENT DOCUMENTS

| | | |
|---|---|---|
| 2011/0282192 A1 | 11/2011 | Axelrod et al. |
| 2012/0070817 A1 | 3/2012 | Wang et al. |
| 2012/0204648 A1 | 8/2012 | Wang et al. |
| 2012/0275262 A1 | 11/2012 | Song et al. |
| 2012/0307250 A1 | 12/2012 | Wang et al. |
| 2013/0245406 A1 | 9/2013 | Wang et al. |
| 2014/0009808 A1 | 1/2014 | Wang et al. |
| 2014/0142404 A1 | 5/2014 | Wang et al. |

FOREIGN PATENT DOCUMENTS

| | | |
|---|---|---|
| JP | 05-126725 A | 5/1993 |
| JP | 2000292416 A | 10/2000 |
| JP | 2009-068977 A | 4/2009 |
| JP | 2010-017426 A | 1/2010 |
| WO | 2006/111929 A1 | 10/2006 |
| WO | 2007/148239 A2 | 12/2007 |
| WO | 2008/062354 A1 | 5/2008 |
| WO | 2008/100386 A2 | 8/2008 |
| WO | 2009/055705 A2 | 4/2009 |
| WO | 2010/048258 A1 | 4/2010 |
| WO | 2010/080991 A2 | 7/2010 |
| WO | 2011/091360 A2 | 7/2011 |
| WO | 2011/127428 A2 | 10/2011 |
| WO | 2013/086293 A1 | 6/2013 |

OTHER PUBLICATIONS

Potter et al., "Capillary Diameter and Geometry in Cardiac and Skeletal Muscle Studied by Means of Corrosion Casts", Microvascular Research, 1983, pp. 68-84, vol. 25.
Robert et al., "Fabrication of focused poly (vinylidene fluoride-trifluoroethylene) P (VDF-TrFE) copolymer 40-50 MHz ultrasound transducers on curved surfaces", Journal of Applied Physics, 2004, pp. 252-256, vol. 96, No. 1.
Saager et al., "Direct characterization and removal of interfering absorption trends in two-layer turbid media", J. Opt. Soc. Am. A, 2005, pp. 1874-1882, vol. 22, No. 9.
Savateeva et al., "Noninvasive detection and staging of oral cancer in vivo with confocal opto-acoustic tomography", Proceedings of SPIE, 2000, pp. 55-66, vol. 3916.
Schmidt et al., "A 32-channel time-resolved instrument for medical optical tomography", Review of Scientific Instruments, 2000, pp. 256-265, vol. 71, No. 1.
Schroeter et al., "Spontaneous slow hemodynamic oscillations are impaired in cerebral microangiopathy", Journal of Cerebral Blood Flow & Metabolism, 2005, pp. 1675-1684, vol. 25.
Sethuraman et al., "Development of a combined intravascular ultrasound and photoacoustic imaging system", Proc. of SPIE, 2006, pp. 60860F-1 through 60860F-10, vol. 6086.
Sethuraman et al., "Intravascular photoacoustic imaging of atherosclerotic plaques: ex vivo study using a rabbit model of atherosclerosis", Proc. of SPIE, 2007, pp. 643729-1 through 643729-9, vol. 6437.
Sheth et al., "Columnar Specificity of Microvascular Oxygenation and Volume Responses: Implications for Functional Brain Mapping", The Journal of Neuroscience, 2004, pp. 634-641, vol. 24, No. 3.
Shmueli et al., "Low-frequency fluctuations in the cardiac rate as a source of variance in the resting-state fMRI BOLD signal", NeuroImage, 2007, pp. 306-320, vol. 38.
Siphanto et al., "Imaging of Small Vessels Using Photoacoustics: An In Vivo Study", Lasers in Surgery and Medicine, 2004, pp. 354-362, vol. 35.
Song et al., "Fast 3-D dark-field reflection-mode photoacoustic microscopy in vivo with a 30-MHz ultrasound linear array", Journal of Biomedical Optics, 2008, pp. 054028 1-054028 5, vol. 13, No. 5.
Song et al., "Section-illumination photoacoustic microscopy for dynamic 3D imaging of microcirculation in vivo", Optics Letters, 2010, pp. 1482-1484, vol. 35, No. 9.

Steinbrink et al., "Illuminating the BOLD signal: combined fMRI-fNIRS studies", Magnetic Resonance Imaging, 2006, pp. 495-505, vol. 24.
Stern, "In vivo evaluation of microcirculation by coherent light scattering", Nature, 1975, pp. 56-58, vol. 254.
Tam, "Applications of photoacoustic sensing techniques", Reviews of Modern Physics, 1986, pp. 381-431 and Figs. 16, 26 and 32, vol. 58, No. 2.
Tearney et al., "Scanning single-mode fiber optic catheter-endoscope for optical coherence tomography", Optics Letters, 1996, pp. 543-545, vol. 21, No. 7.
Tran et al., "In vivo endoscopic optical coherence tomography by use of a rotational microelectromechanical system probe", Optics Letters, 2004, pp. 1236-1238, vol. 29, No. 11.
Van Essen et al., "An Integrated Software Suite for Surface-based Analyses of Cerebral Cortex", Journal of the American Medical Informatics Association, 2001, pp. 443-459, vol. 8, No. 5.
Viator et al., "Design and testing of an endoscopic photoacoustic probe for determination of treatment depth after photodynamic therapy", SPIE Proceedings in Biomedical Optoacoustics II, 2001, pp. 16-27, vol. 4256.
Wang et al., "Ballistic 2-D Imaging Through Scattering Walls Using an Ultrafast Optical Kerr Gate", Science, 1991, pp. 769-771, vol. 253.
Wang et al., "MCML—Monte Carlo modeling of light transport in multi-layered tissues", Computer Methods and Programs in Biomedicine, 1995, pp. 131-146, vol. 47.
Wang et al., "Noninvasive laser-induced photoacoustic tomography for structural and functional in vivo imaging of the brain", Nature Biotechnology, 2003, pp. 803-806, vol. 21, No. 7.
Wang et al., "Three-dimensional laser-induced photoacoustic tomography of mouse brain with the skin and skull intact", Optics Letters, 2003, pp. 1739-1741, vol. 28, No. 19.
Wang et al., "Noninvasive photoacoustic angiography of animal brains in vivo with near-infrared light and an optical contrast agent", Optics Letters, 2004, pp. 730-732, vol. 29, No. 7.
Wang et al., "Biomedical Optics, Principles and Imaging", 2007, Wiley-Interscience, A John Wiley & Sons, Inc., Hoboken, New Jersey, US, 7 pgs.
Wang, "Multiscale photoacoustic microscopy and computed tomography", Nature Photonics, 2009, pp. 503-509, vol. 3.
Wang et al., "Intravascular Photoacoustic Imaging", IEEE Journal of Selected Topics in Quantum Electronics, 2010, pp. 588-599, vol. 16, No. 3.
Xu et al., "Photoacoustic imaging in biomedicine", Review of Scientific Instruments, 2006, pp. 041101 1-041101 22, vol. 77.
Xu et al., "Time Reversal Ultrasound Modulated Optical Tomography Using a BSO Phase Conjugate Mirror", poster presented at SPIE Conference 7177 on Jan. 26, 2009; 3 pgs.
Yadlowsky et al., "Multiple scattering in optical coherence microscopy", Applied Optics, 1995, pp. 5699-5707, vol. 34, No. 25.
Yang et al., "Optical coherence and Doppler tomography for monitoring tissue changes induced by laser thermal therapy—An in vivo feasibility study", Review of Scientific Instruments, 2003, pp. 437-440, vol. 74, No. 1.
Yang et al., "Novel biomedical imaging that combines intravascular ultrasound (IVUS) and optical coherence tomography (OCT)", IEEE International Ultrasonics Symposium Proceedings, 2008, pp. 1769-1772.
Yao et al., "Monte Carlo simulation of an optical coherence tomography signal in homogeneous turbid media", Phys. Med. Biol., 1999, pp. 2307-2320, vol. 44.
Yaqoob et al., "Methods and application areas of endoscopic optical coherence tomography", Journal of Biomedical Optics, 2006, pp. 063001-1 through 063001-19, vol. 11, No. 6.
Yodh et al., "Spectroscopy and Imaging With Diffusing Light", Physics Today, Mar. 1995, pp. 34-40.
Yodh et al., "Functional Imaging with Diffusing Light", Biomedical Photonics Handbook, 2003, Chapter 21, 45 pgs., CRC Press, Boca Raton.
Zeff et al., "Retinotopic mapping of adult human visual cortex with high-density diffuse optical tomography", Proceedings of the National Academy of Sciences, 2007, pp. 12169-12174, vol. 104, No. 29.

(56) References Cited

OTHER PUBLICATIONS

Zemp et al., "Realtime photoacoustic microscopy in vivo with a 30-MHz ultrasonic array transducer", Optics Express, 2008, pp. 7915-7928, vol. 16, No. 11.
Zhang et al., "Functional photoacoustic microscopy for high-resolution and noninvasive in vivo imaging", Nature Biotechnology, 2006, pp. 848-851, vol. 24, No. 7.
Zhang et al., "In vivo imaging of subcutaneous structures using functional photoacoustic microscopy", Nature Protocols, 2007, pp. 797-804, vol. 2, No. 4.
Zhang et al., "Intrinsic Functional Relations Between Human Cerebral Cortex and Thalamus", J Neurophysiol, 2008, pp. 1740-1748, vol. 100.
Zharov et al., "In vivo photoacoustic flow cytometry for monitoring of circulating single cancer cells and contrast agents", Optics Letters, 2006, pp. 3623-3625, vol. 31, No. 24.
Zou et al., "BOLD response to visual stimulation in survivors of childhood cancer", NeuroImage, 2005, pp. 61-69, vol. 24.
Al et al., "Spectral-domain optical coherence tomography: Removal of autocorrelation using an optical switch", Applied Physics Letters, 2006, pp. 111115-1-111115-3, vol. 88.
Allen et al., "Pulsed near-infrared laser diode excitation system for biomedical photoacoustic imaging", Optics Letters, 2006, pp. 3462-3464, vol. 31, No. 23.
Bell, "On the Production and Reproduction of Sound by Light", American Journal of Sciences, Third Series, Oct. 1880, pp. 305-324, vol. XX.
Calasso et al., "Photoacoustic Point Source", Physical Review Letters, 2001, pp. 3550-3553, vol. 86, No. 16.
Cannata et al., "Development of a 35-MHz Piezo-Composite Ultrasound Array for Medical Imaging", IEEE Transactions on Ultrasonics, Ferroelectrics, and Frequency Control, 2006, pp. 224-236, vol. 53, No. 1.
Cheong et al., "A Review of the Optical Properties of Biological Tissues", IEEE Journal of Quantum Electronics, 1990, pp. 2166-2185, vol. 26, No. 12.
D'Andrea et al., "Time-resolved optical imaging through turbid media using a fast data acquisition system based on a gated CCD camera", Journal of Physics D: Applied Physics, 2003, pp. 1675-1681, vol. 36.
de Boer et al., "Improved signal-to-noise ratio in spectral-domain compared with time-domain optical coherence tomography", Optics Letters, 2003, pp. 2067-2069, vol. 28, No. 21.
Diebold et al., "Photoacoustic "Signatures" of Particulate Matter: Optical Production of Acoustic Monopole Radiation", Science, New Series, 1990, pp. 101-104, vol. 250, No. 4977.
Diebold et al., "Photoacoustic Monopole Radiation in One, Two, and Three Dimensions", Physical Review Letters, 1991, pp. 3384-3387 and Figs. 1 and 2, vol. 26, No. 24.
Dunn et al., "Transport-based image reconstruction in turbid media with small source-detector separations", Optics Letters, 2000, pp. 1777-1779, vol. 25, No. 24.
Ermilov et al., "Laser optoacoustic imaging system for detection of breast cancer", Journal of Biomedical Optics, 2009, pp. 024007 1-024007 14, vol. 14, No. 2.
Erpelding et al., "Sentinel Lymph Nodes in the Rat: Noninvasive Photoacoustic and US Imaging with a Clinical US System", Radiology, 2010, pp. 102-110, vol. 256, No. 1.
Extended European Search Report from European Patent Application No. 08842292.8, dated Dec. 17, 2013, 8 pgs.
Fan et al., "Development of a laser photothermoacoustic frequency-swept system for subsurface imaging: Theory and experiment", J. Acoust. Soc. Am., 2004, pp. 3523-3533, vol. 116, No. 6.
Fang et al., "Photoacoustic Doppler Effect from Flowing Small Light-Absorbing Particles", Physical Review Letters, 2007, pp. 184501 1-184501 4, vol. 99.
Fercher et al., "Measurement of intraocular distances by backscattering spectral interferometry", Optics Communications, 1995, pp. 43-48, vol. 117.
Foster et al., "Advances in Ultrasound Biomicroscopy", Ultrasound in Medicine and Biology, 2000, pp. 1-27, vol. 26, No. 1.
Gibson et al., "Recent advances in diffuse optical imaging", Physics in Medicine and Biology, 2005, pp. R1-R43, vol. 50.
Guittet et al., "In Vivo High-Frequency Ultrasonic Characterization of Human Dermis", IEEE Transactions on Biomedical Engineering, 1999, pp. 740-746, vol. 46, No. 6.
Hebden et al., "Enhanced time-resolved imaging with a diffusion model of photon transport", Optics Letters, 1994, pp. 311-313, vol. 19, No. 5.
Hee et al., "Femtosecond transillumination tomography in thick tissues", Optics Letters, 1993, pp. 1107-1109, vol. 18, No. 13.
Hillman et al., "Laminar optical tomography: demonstration of millimeter-scale depth-resolved imaging in turbid media", Optics Letters, 2004, pp. 1650-1652, vol. 29, No. 14.
Hoelen et al., "Three-dimensional photoacoustic imaging of blood vessels in tissue", Optics Letters, 1998, pp. 648-650, vol. 23, No. 8.
Hu et al., "Label-free photoacoustic ophthalmic angiography", Optics Letters, 2010, pp. 1-3, vol. 35, No. 1.
Huang et al., "Optical Coherence Tomography", Science, New Series, 1991, pp. 1178-1181, vol. 254, No. 5035.
Huber et al., "Three-dimensional and C-mode OCT imaging with a compact, frequency swept laser source at 1300 nm", Optics Express, 2005, pp. 10523-10538, vol. 13, No. 26.
ISR and Written Opinion from related International Application No. PCT/US2008/081167, dated Apr. 22, 2009; 7 pgs.
ISR and Written Opinion from related International Application No. PCT/US2009/061435, dated Mar. 29, 2010; 10 pgs.
ISR and Written Opinion from related International Application No. PCT/US2010/020488, dated Aug. 31, 2010; 10 pgs.
ISR and Written Opinion from related International Application No. PCT/US2011/022253, dated Sep. 22, 2011; 8 pgs.
ISR and Written Opinion from related International Application No. PCT/US2011/031823, dated Dec. 26, 2011; 8 pgs.
ISR and Written Opinion from related International Application No. PCT/US2012/068403, dated Mar. 19, 2013; 10 pgs.
Karamata et al., "Multiple scattering in optical coherence tomography. I. Investigation and modeling", Journal Optical Society of America, 2005, pp. 1369-1379, vol. 22, No. 7.
Kim et al., "In Vivo Molecular Photoacoustic Tomography of Melanomas Targeted by Bioconjugated Gold Nanocages", Acs Nano, 2010, pp. 4559-4564, vol. 4, No. 8.
Kolkman et al., "In Vivo Photoacoustic Imaging of Blood Vessels Using an Extreme-Narrow Aperture Sensor", IEEE Journal of Selected Topics in Quantum Electronics, 2003, pp. 343-346, vol. 9, No. 2.
Kruger et al., "Photoacoustic ultrasound (PAUS)—Reconstruction tomography", Med. Phys., 1995, pp. 1605-1609, vol. 22, No. 10.
Kruger et al., "Thermoacoustic computed tomography—technical considerations", Medical Physics, 1999, pp. 1832-1837, vol. 26, No. 9.
Kruger et al., "Breast Cancer in Vivo: Contrast Enhancement with Thermoacoustic CT at 434 MHz—Feasibility Study", Radiology, 2000, pp. 279-283, vol. 216, No. 1.
Kruger et al., "Thermoacoustic computed tomography using a conventional linear transducer array", Medical Physics, 2003, pp. 856-860, vol. 30, No. 5.
Kruger et al., "Thermoacoustic Optical Molecular Imaging of Small Animals", Molecular Imaging, 2003, pp. 113-123, vol. 2.
Ku et al., "Scanning thermoacoustic tomography in biological tissue", Medical Physics, 2000, pp. 1195-1202, vol. 27, No. 5.
Ku et al., "Scanning microwave-induced thermoacoustic tomography: Signal, resolution, and contrast", Medical Physics, 2001, pp. 4-10, vol. 28, No. 1.
Ku et al., "Multiple-bandwidth photoacoustic tomography", Physics. Med. Biol., 2004, pp. 1329-1338, vol. 49, No. 7.
Ku et al., "Deeply penetrating photoacoustic tomography in biological tissues enhanced with an optical contrast agent", Optics Letters, 2005, pp. 507-509, vol. 30, No. 5.
Ku et al., "Imaging of tumor angiogenesis in rat brains in vivo by photoacoustic tomography", Applied Optics, 2005, pp. 770-775, vol. 44, No. 5.

(56) References Cited

OTHER PUBLICATIONS

Ku et al., "Thermoacoustic and Photoacoustic Tomography of Thick Biological Tissues Toward Breast Imaging", Technology in Cancer Research & Treatment, 2005, pp. 559-566, vol. 4, No. 5.
Leitgeb et al., "Performance of fourier domain vs. time domain optical coherence tomography", Optics Express, 2003, pp. 889-894, vol. 11, No. 8.
Li et al., "Optical coherence computed tomography", Applied Physics Letters, 2007, pp. 141107-1-141107-3, vol. 91.
Li et al., "Simultaneous Molecular and Hypoxia Imaging of Brain Tumors In Vivo Using Spectroscopic Photoacoustic Tomography", Proceedings of the IEEE, 2008, pp. 481-489, vol. 96, No. 3.
Manohar et al., "Initial Results of in vivo non-invasive cancer imaging in the human breast using near-infrared photoacoustics", Optics Express, 2007, pp. 12277-12285, vol. 15, No. 19.
Maslov et al., "In vivo dark-field reflection-mode photoacoustic microscopy", Optics Letters, 2005, pp. 625-627, vol. 30, No. 6.
Maslov et al., "Photoacoustic imaging of biological tissue with intensity-modulated continuous-wave laser", Journal of Biomedical Optics, 2008, pp. 024006 1-024006 5, vol. 13, No. 2.
Maslov et al., "Optical-resolution photoacoustic microscopy for in vivo imaging of single capillaries", Optical Letters, 2008, pp. 929-931, vol. 33, No. 9.
Mishra et al., "Development and comparison of the DTM, the DOM and the FVM formulations for the short-pulse laser transport through a participating medium", International Journal of Heat and Mass Transfer, 2006, pp. 1820-1832, vol. 49.
Morgner et al., "Spectroscopic optical coherence tomography", Optics Letters, 2000, pp. 111-113, vol. 25, No. 2.
Murray et al., "High-sensitivity laser-based acoustic microscopy using a modulated excitation source", Applied Physics Letters, 2004, pp. 2974-2976, vol. 85, No. 14.
Nakajima et al., "Three-Dimensional Analysis and Classification of Arteries in the Skin and Subcutaneous Adipofascial Tissue by Computer Graphics Imaging", Plastic and Reconstructive Surgery, 1998, pp. 748-760, vol. 102, No. 3.
Nelson et al., "Imaging Glioblastoma Multiforme", The Cancer Journal, 2003, pp. 134-145, vol. 9, No. 2.
Niederhauser et al., "Combined Ultrasound and Optoacoustic System for Real-Time High-Contrast Vascular Imaging in Vivo", IEEE Transactions on Medical Imaging, 2005, pp. 436-440, vol. 24, No. 4.
Office Action from related U.S. Appl. No. 13/574,994, dated Aug. 26, 2014; 10 pgs.
Office Action from related U.S. Appl. No. 13/574,994, dated Mar. 17, 2014; 9 pgs.
Notice of Allowance from related U.S. Appl. No. 12/739,589, dated Feb. 5, 2013; 9 pgs.
Office Action from related U.S. Appl. No. 12/739,589, dated Jul. 19, 2012; 9 pgs.
Notice of Allowance from related U.S. Appl. No. 12/254,643, dated Nov. 22, 2010; 8 pgs.
Office Action from related U.S. Appl. No. 12/254,643, dated Aug. 6, 2010; 9 pgs.
Notice of Allowance from related U.S. Appl. No. 13/369,558, dated Jul. 29, 2014; 7 pgs.
Office Action from related U.S. Appl. No. 13/369,558, dated Jun. 20, 2014; 10 pgs.
Office Action from related U.S. Appl. No. 11/625,099, dated Nov. 1, 2010; 11 pgs.
Office Action from related U.S. Appl. No. 11/625,099, dated Apr. 20, 2010; 11 pgs.
Office Action from related U.S. Appl. No. 13/450,793, dated Aug. 1, 2014; 21 pgs.
Office Action from related U.S. Appl. No. 13/450,793, dated Mar. 24, 2014; 22 pgs.
Office Action from related U.S. Appl. No. 13/450,793, dated Nov. 22, 2013; 22 pgs.
Office Action from related U.S. Appl. No. 13/450,793, dated Jun. 5, 2013; 20 pgs.
Notice of Allowance from related U.S. Appl. No. 12/568,069, dated Feb. 22, 2013; 7 pgs.
Office Action from related U.S. Appl. No. 12/568,069, dated Dec. 21, 2012; 10 pgs.
Office Action from related U.S. Appl. No. 12/568,069, dated Sep. 18, 2012; 14 pgs.
Office Action from related U.S. Appl. No. 12/568,069, dated Mar. 29, 2012; 10 pgs.
Office Action from related U.S. Appl. No. 13/143,832, dated Apr. 18, 2014; 14 pgs.
Office Action from related U.S. Appl. No. 13/125,522, dated Oct. 29, 2014; 10 pgs.
Office Action from related U.S. Appl. No. 13/125,522, dated Jul. 17, 2014; 10 pgs.
Office Action from related U.S. Appl. No. 13/125,522, dated May 23, 2013; 10 pgs.
Office Action from related U.S. Appl. No. 13/125,522, dated Jan. 22, 2013; 8 pgs.
Office Action from related U.S. Appl. No. 13/874,653, dated Nov. 5, 2014; 6 pgs.
Oraevsky et al., "Laser Optoacoustic Tomography of Layered Tissues: Signal Processing", SPIE, 1997, pp. 59-70, vol. 2979.
Oraevsky et al., "Laser Opto-Acoustic Imaging of the Breast: Detection of Cancer Angiogenesis", Proc. SPIE, 1999, pp. 352-363, vol. 3597, No. 56.
Oraevsky et al., "Ultimate Sensitivity of Time-Resolved Opto-Acoustic Detection", Biomedical Optoacoustics, Proceedings of SPIE, 2000, pp. 228-239, vol. 3916.
Oraevsky et al., "Optoacoustic Tomography", Biomedical Photonics Handbook, 2003, pp. 1-40, CRC Press LLC, USA.

\* cited by examiner

QUANTIFICATION OF OPTICAL ABSORPTION COEFFICIENTS USING ACOUSTIC SPECTRA IN PHOTOACOUSTIC TOMOGRAPHY

CROSS REFERENCE TO RELATED APPLICATIONS

This application claims the benefit of U.S. Provisional Patent Application No. 61/322,605 filed Apr. 9, 2010, which is hereby incorporated by reference in its entirety.

STATEMENT REGARDING FEDERALLY SPONSORED RESEARCH & DEVELOPMENT

This invention was made with government support under grant R01 EB008085, awarded by the U.S. National Institutes of Health. The government has certain rights in the invention.

BACKGROUND

The embodiments described herein relate generally to photoacoustic scanning methods and apparatus and, more particularly, to a method and a system for determining an optical absorption coefficient by an object using acoustic spectra.

Total, oxygenated, and deoxygenated hemoglobin concentrations ([HbT], [HbO$_2$], and [HbR], respectively) are fundamental pathophysiological parameters in biomedicine. For example, abnormally low [HbT] may be caused by loss of blood, nutritional deficiency, chemotherapy, inflammation, kidney failure or bone marrow problems, while abnormally high [HbT] may be related to exposure to high altitude, smoking, dehydration and tumors. Blood oxygen saturation (sO$_2$), which is defined as [HbO$_2$] divided by [HbT], is vital in understanding brain hemodynamics in response to sensory stimulations, monitoring healing of burns and wounds, and evaluating the effectiveness of chemotherapy and radiotherapy on tumors. Several techniques have been developed to quantify hemoglobin concentration and sO$_2$ in vivo, including near-infrared spectroscopy (NIRS), blood oxygen level dependent (BOLD) contrast magnetic resonance imaging (MRI), electron paramagnetic resonance imaging (EPRI), positron emission tomography (PET), and single photon emission computed tomography (SPECT). However, all of these modalities have disadvantages. For example, at least some of these modalities have poor spatial resolution, relative quantification, and undesirable contrast agent injection. Photoacoustic (PA) tomography (PAT) has already demonstrated its ability to monitor biological hemodynamic functions without using exogenous contrast agents. Quantitative PAT is challenging, because compensating for the fluence in quantitative in vivo photoacoustic tomography is difficult, and factors, such as the tissue acoustic attenuation and the imaging system bandwidth, also affect the quantification accuracy.

BRIEF DESCRIPTION

In one aspect, a photoacoustic imaging method includes illuminating an object using a light beam emitted by a light source, and detecting a pressure wave emitted by the object using an acoustic transducer, wherein the pressure wave is induced by the object in response to the light beam (e.g., light pulse). The object is illuminated with at least two light pulses having different wavelengths, and the absorption coefficient of the object is determined from the detected pressure waves. The method also includes calculating an amount of optical energy that is absorbed by the object from the light beam, based at least on the pressure.

BRIEF DESCRIPTION OF THE DRAWINGS

The embodiments described herein may be better understood by referring to the following description in conjunction with the accompanying drawings.

DETAILED DESCRIPTION

Figure 1:
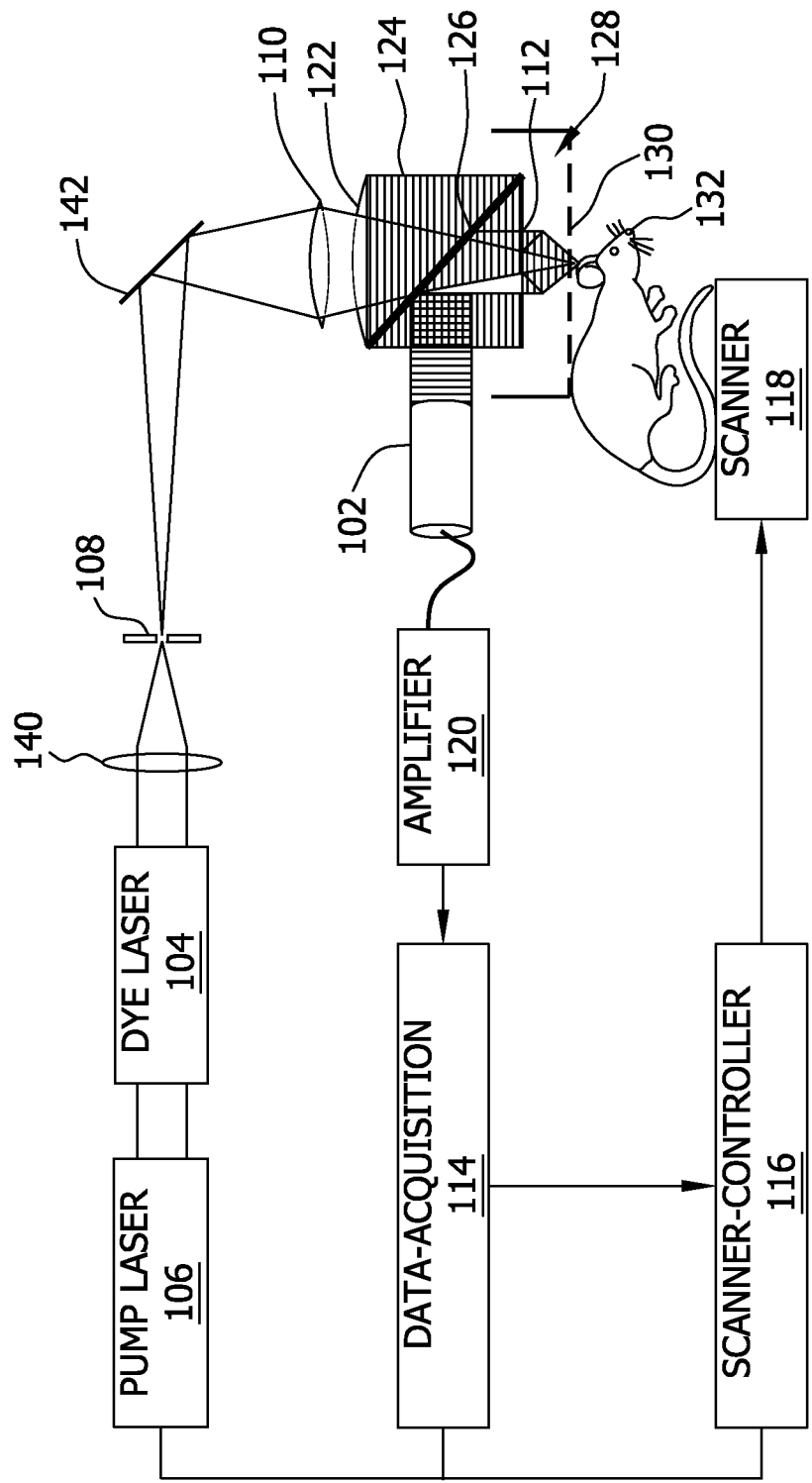
FIG. 1 is a schematic diagram of an exemplary optical resolution photoacoustic microscopy (OR-PAM) system.

While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not delimit the scope of the disclosure.

To facilitate the understanding of the embodiments described herein, a number of terms are defined below. The terms defined herein have meanings as commonly understood by a person of ordinary skill in the areas relevant to the present disclosure. Terms such as "a," "an," and "the" are not intended to refer to only a singular entity, but rather include the general class of which a specific example may be used for illustration. The terminology herein is used to describe specific embodiments of the disclosure, but their usage does not delimit the disclosure, except as outlined in the claims.

To be consistent with the commonly used terminology, whenever possible, the terms used herein will follow the definitions recommended by the Optical Society of America (OCIS codes).

In some embodiments, the term "photoacoustic microscopy" refers generally to a photoacoustic imaging technology that detects pressure waves generated by light absorption in the volume of a material (such as biological tissue) and propagated to the surface of the material. In other words, photoacoustic microscopy is a method for obtaining three-dimensional images of the optical contrast of a material by detecting acoustic or pressure waves traveling from the object. Imaging resolution is on the micrometer scale.

In some embodiments, the term "photoacoustic tomography" also refers to a photoacoustic imaging technology that detects acoustic or pressure waves generated by light absorption in the volume of a material (such as biological tissue) and propagated to the surface of the material. The emphasis is sometimes on photoacoustic computed tomography, i.e., cross-sectional or three-dimensional photoacoustic imaging based on computer reconstruction, although the most general definition of photoacoustic tomography encompasses photoacoustic microscopy.

In some embodiments, the terms "reflection mode" and "transmission mode" refer generally to a laser photoacoustic microscopy system that employs the detection of acoustic or pressure waves transmitted from the volume of their generation to the optically irradiated surface and a surface that is opposite to, or substantially different from, the irradiated surface, respectively.

In some embodiments, the term "time-resolved detection" refers generally to the recording of the time history of a pressure wave with a temporal resolution sufficient to reconstruct the pressure wave profile.

In some embodiments, the term "photoacoustic waves" refers generally to pressure waves produced by light absorption.

In photoacoustic imaging, a sample is illuminated, usually by a pulsed laser, and following the absorption of optical energy, an initial pressure is generated via thermo-elastic expansion. The photoacoustic waves then propagate and are detected by acoustic or ultrasonic sensors. The strength of the initial pressure is directly proportional to the absorbed optical energy in the tissue and, therefore, multi-wavelength photoacoustic measurements may yield optical absorption spectral information. Since ultrasound scattering is much weaker than optical scattering in biological tissues, photoacoustic tomography is capable of high resolution imaging at depths beyond the optical transport mean free path. Moreover, because photoacoustic imaging inherently exploits optical absorption contrast, it usually has a higher sensitivity to optical absorption than other optical imaging technologies. By measuring the optical absorption spectrum with photoacoustic imaging, $sO_2$ may be quantified in the same way near infrared spectroscopy (NIRS) quantifies $sO_2$, except with high spatial resolution and sensitivity.

Photoacoustic images are spatial mappings of the absorbed optical energy $A(\vec{r})$ (Jm$^{-3}$), which is the product of the optical absorption coefficient $\mu_a(\vec{r},\lambda)$ (m$^{-1}$) and the fluence $F(\vec{r})$ (Jm$^{-2}$). To obtain the intrinsic tissue property $\mu_a(\vec{r},\lambda)$, there is a need to compensate for the extrinsic quantity $F(\vec{r})$. Since the optical parameters for tissues are usually heterogeneous and unknown, the fluence varies from case to case and is difficult to model. As a consequence, compensating for the fluence in quantitative in vivo photoacoustic tomography is a challenge.

Currently, fluence compensation can be done invasively or non-invasively. The invasive method includes positioning an optical absorber with a known spectrum close to the region of interest, and then normalizing the measured photoacoustic signals from the objects with the amplitudes of the photoacoustic signals from the optical absorber having a known spectrum. Alternatively, the incident fluence may be estimated by measuring light transmission through a sample of excised tissue of the same type as the tissue overlaying a region of interest. The non-invasive method involves solving the radiative transfer equation (RTE) and photoacoustic wave equations with iterative algorithms. Both of these methods are based on the linear relationship between the local fluence incident on the blood vessel, acquired either by experimental measurements or numerical simulation, and the peak amplitude of the photoacoustic signal.

A temporal profile of the photoacoustic signal is used to quantify the optical absorption coefficients. This temporal method is self-calibrating since it depends on the relative temporal profile rather than the absolute amplitude of the photoacoustic signal. Therefore, the temporal profile is less dependent on changes in the optical properties of overlying tissues. However, since the temporal profile is distorted by various factors, such as the limited bandwidth of acoustic detectors and frequency-dependent acoustic attenuation of the sample or region of interest, linear translation of the temporal profile to the optical absorption may be inaccurate.

As will be described in greater detail below, embodiments of the present disclosure provide a method for quantifying the optical absorption coefficient using the acoustic spectra of the photoacoustic signals. By carefully investigating the factors involved in generating the acoustic spectrum, the effects of detector bandwidth and acoustic attenuation are eliminated, as shown later. At least some embodiments of the method are self-calibrating since it deals only with the relative change in various acoustic frequencies. The acoustic spectrum $S(\omega)$ of the received photoacoustic signal depends on three factors: 1) the 'real' object spectrum $O(\omega,\lambda)$ measured with unit fluence, which is related to the target object's shape, size, optical properties, and fluence incident directions; 2) the system dependent response $H(\omega)$, which is the Fourier transform of the photoacoustic signal from an ideal point absorber measured with this system without acoustic attenuation in the tissue; and 3) the tissue related acoustic attenuation effect $a(\omega)$, which is related to the acoustic properties of the tissue that lies between the target objects (e.g., region of interest) and the detector. Based on a system linearity assumption, the above factors lead to the expression $S(\omega,\lambda)=F(\lambda)O(\omega,\lambda)H(\omega)a(\omega)$. The last two terms remain unchanged when samples are measured with the same system under the same condition, and therefore are usually cancelable. An example is where light at various optical wavelengths is used to excite one blood vessel. Therefore, by dividing the photoacoustic acoustic spectrum measured at one optical wavelength by the spectrum measured at another wavelength, the system dependent effects and the acoustic attenuation effect may be eliminated. As such, the absolute value of $\mu_a$ may be quantified with this method even though F varies with the optical wavelength. By contrast, previous methods can quantify only the relative value of $\mu_a$.

Figure 2:
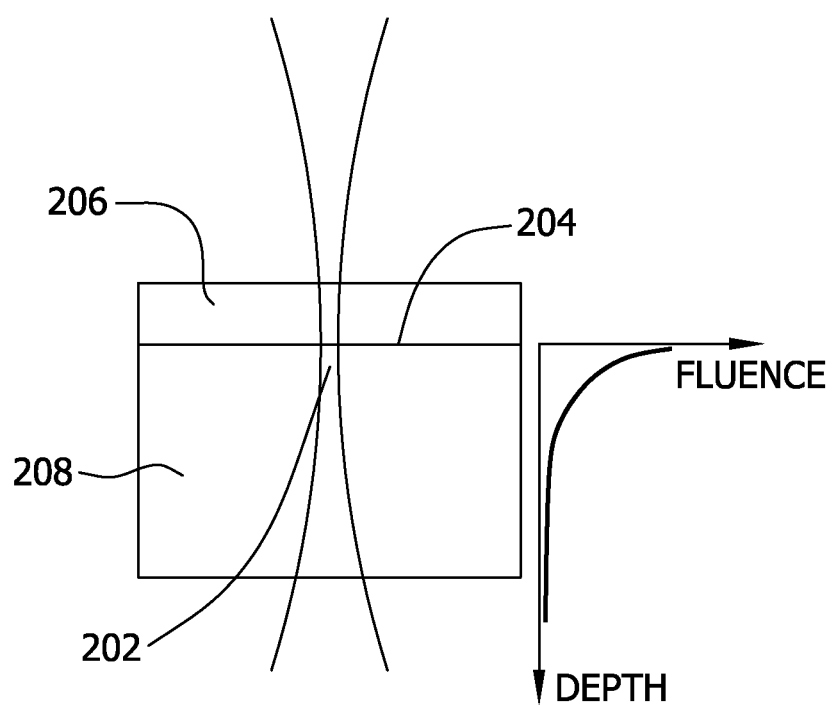
FIG. 2 is a diagram of an exemplary experimental setup of a sample for OR-PAM.

As a feasibility study, this idea has been implemented and validated using one form of photoacoustic imaging, optical resolution photoacoustic microscopy (OR-PAM), where the object spectrum $O(\omega,\lambda)$ may be relatively easily modeled. Referring to FIG. 1, in OR-PAM, photoacoustic A-scan signals are acquired through time-resolved acoustic detection, and three-dimensional images are formed by raster scanning the acoustic transducer 102 along the transverse plane, as shown in FIG. 1. The axial resolution of the system depended on the transducer bandwidth (centered at 50 MHz with 80% bandwidth), while the lateral resolution relied on optical focusing, which can reach the theoretical optical diffraction limit. For the system of FIG. 1, the axial and lateral resolutions were quantified to be approximately 15 micrometers (μm) and approximately 5 μm, respectively. Therefore, the surface of blood vessels with a diameter of greater than approximately 30 μm may be roughly treated as a flat surface. In this case, the acoustic spectrum of the generated photoacoustic signal is only related to the optical penetration depth. If $F_0$ is used to denote the incident fluence on the surface of the blood vessel, the fluence inside the blood vessel obeys Beer's law and may be written as $F(z)=F_0 \exp(-\mu_a z)$, as shown in FIG. 2. Here, the reduced scattering coefficient is much less than the absorption coefficient, because the anisotropy factor is so close to 1 in blood in the optical spectral region that was used (around 585 nm); therefore, it is neglected. The photoacoustic signal generated by the object is expressed using Equation (1):

$$O(t,\lambda) = \mu_a(\lambda) \exp[-\mu_a(\lambda)ct] \quad \text{Eq. (1)}$$

where c is the speed of sound in the biological tissue. Performing a Fourier transformation of Eq. (1) leads to Equation (2):

$$|O(\omega, \lambda)| = \frac{1}{\sqrt{[\omega/\mu_a(\lambda)]^2 + c^2}} \quad \text{Eq. (2)}$$

Moreover, if the photoacoustic signals of the blood vessel are measured at two optical wavelengths, the ratio of the spectra of the photoacoustic signals may be written as shown in Equation (3):

$$\frac{S(\omega, \lambda_1)}{S(\omega, \lambda_2)} = \frac{F(\lambda_1)O(\omega, \lambda_1)H(\omega)a(\omega)}{F(\lambda_2)O(\omega, \lambda_2)H(\omega)a(\omega)} = \frac{F(\lambda_1)\sqrt{[\omega/\mu_a(\lambda_2)]^2 + c^2}}{F(\lambda_2)\sqrt{[\omega/\mu_a(\lambda_1)]^2 + c^2}} \quad \text{Eq. (3)}$$

Furthermore, the absolute values of $\mu_a(\lambda_1)$, $\mu_a(\lambda_2)$, and $F(\lambda_1)/F(\lambda_2)$ may be derived by fitting the ratio of Eq. (3). The assumption of laser beam collimation within the blood vessel for Eqs. (1)-(3) is valid within and far from the optical focal zone. Otherwise, the 3D Gaussian beam profile should be considered. Here, the Rayleigh range of the Gaussian beam is approximately 30 μm, which is comparable to the optical penetration depth in blood around 585 nm.

Figure 3:
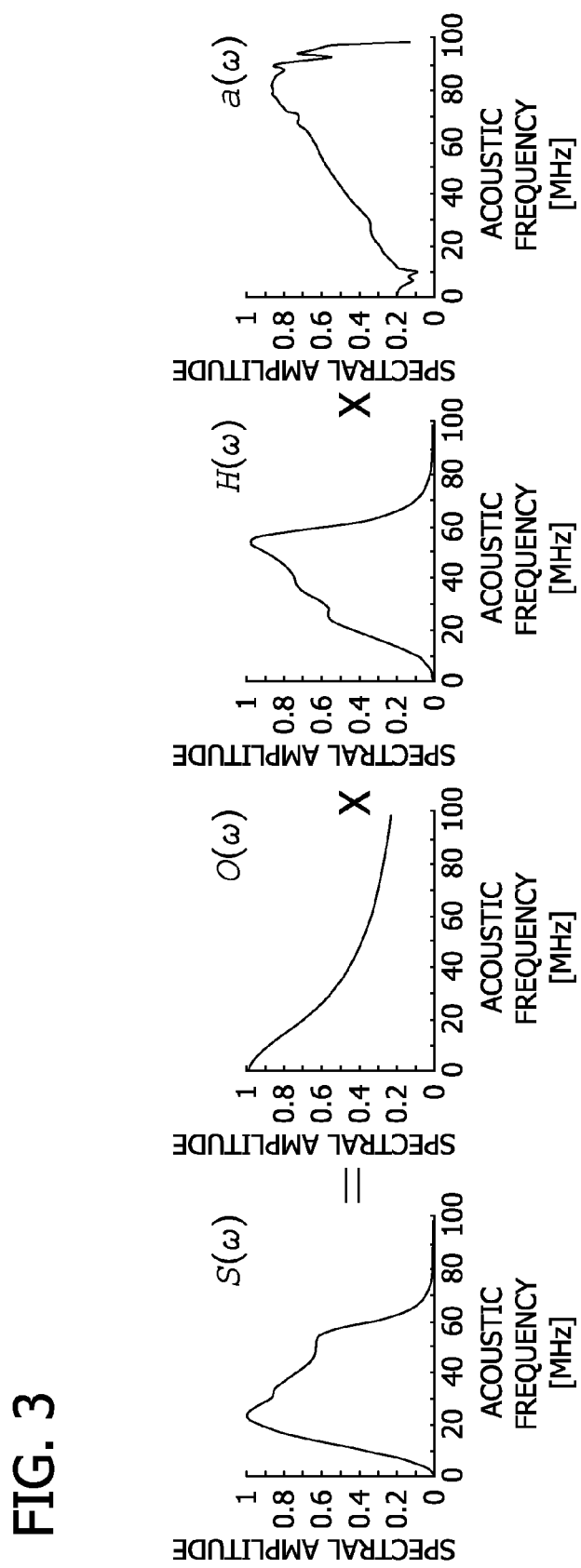
FIG. 3 is a set of graphs that illustrate an example of an object spectrum O($\omega,\lambda$), a system dependent response H($\omega$), and a tissue-related acoustic attenuation effect a($\omega$) acquired via the OR-PAM system of FIGS. 1 and 2.

FIG. 1 is a schematic diagram of an exemplary OR-PAM system, FIG. 2 is a diagram of an exemplary experimental setup, and FIG. 3 is a set of graphs that illustrate an example of O(ω,λ), H(ω), and a(ω). The system includes a dye laser 104 pumped by a Nd:YLF laser 106 that is used as the irradiation source. The laser beam from the dye laser 104 passes through a condenser lens 140, is spatially filtered by a pinhole 108, is redirected by a mirror 142, and is then focused by an objective lens 110. Sonic and ultrasonic focusing is achieved through a plano-concave lens 112. The optical objective lens 110 and 50 MHz acoustic transducer 102 are confocally configured via a correction lens 122, a right angle prism 124, and a silicone oil layer 126. A water tank 128 and membrane 130 separate the acoustic lens 112 from the sample 132. Volumetric images are generated by data acquisition device 114 through a combination of time-resolved detection of the photoacoustic waves with a two-dimensional raster scanning in the transverse plane. A scanner controller 116 and scanner 118 (i.e., two dimensional motivator platform) provide rasterizing under the control of data acquisition device 114, and the data acquisition device 114 receives data from acoustic transducer 102 via amplifier 120. The data acquisition device 114 provides a trigger signal to the pump laser 106 and the scanner controller 116 and also provides a clock signal to the scanner controller 116. The trigger and clock signals initiate and control the timing of light pulses from the pump laser 106 and dye laser 104 in coordination with movement of the scanner 118.

As shown in FIG. 2, the optical focus 202 of the system of FIG. 1 is much smaller than a targeted blood vessel whose top surface 204 within the optical focal diameter can therefore be approximated as a plane. An overlying tissue 206 covers the blood vessel top surface 204, and blood 208 lies beneath the blood vessel top surface 204 in the setup of FIGS. 1 and 2. The optical fluence within the blood vessel decays exponentially with depth at a rate of the optical absorption coefficient. FIG. 3 is an example of the object spectrum O(ω,λ), the system dependent response H(ω), and the tissue related acoustic attenuation effect a(ω).

Figure 4:
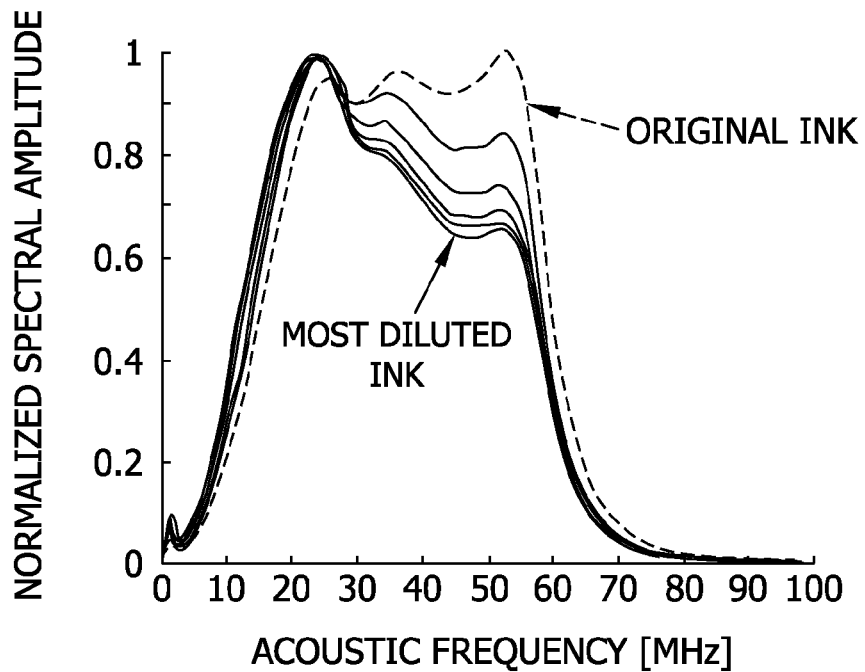
FIG. 4 is a graph illustrating acoustic spectra of a number of photoacoustic signals.
Figure 5:
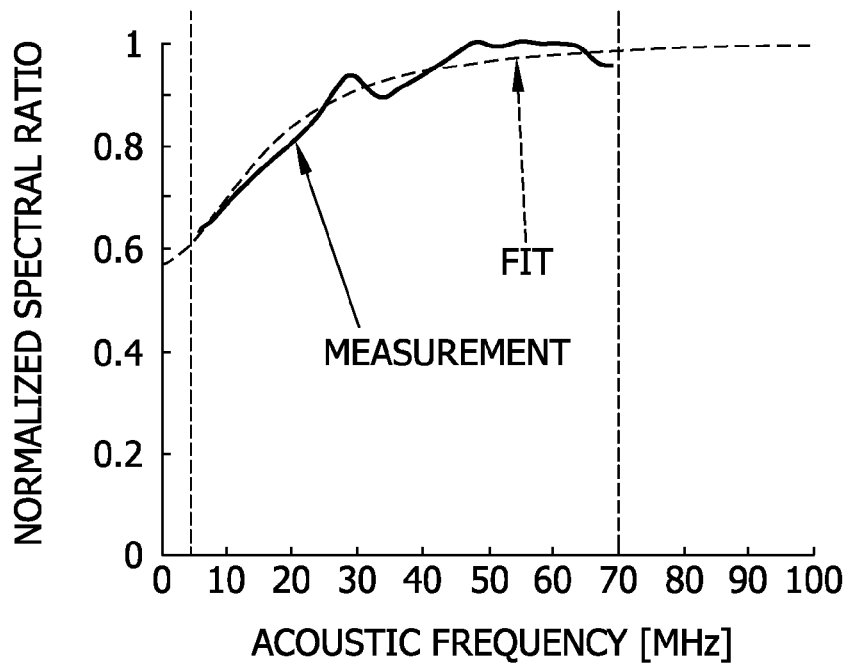
FIG. 5 is a graph illustrating a comparison of photoacoustic spectra of two objects.
Figure 6:
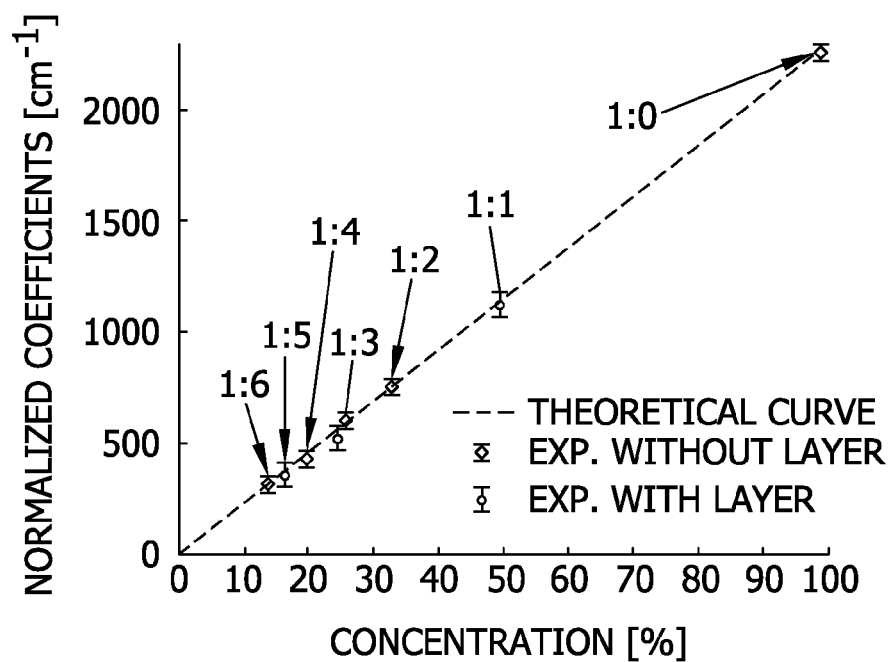
FIG. 6 is a graph illustrating quantified absorption coefficients of a plurality of samples.
Figure 7:
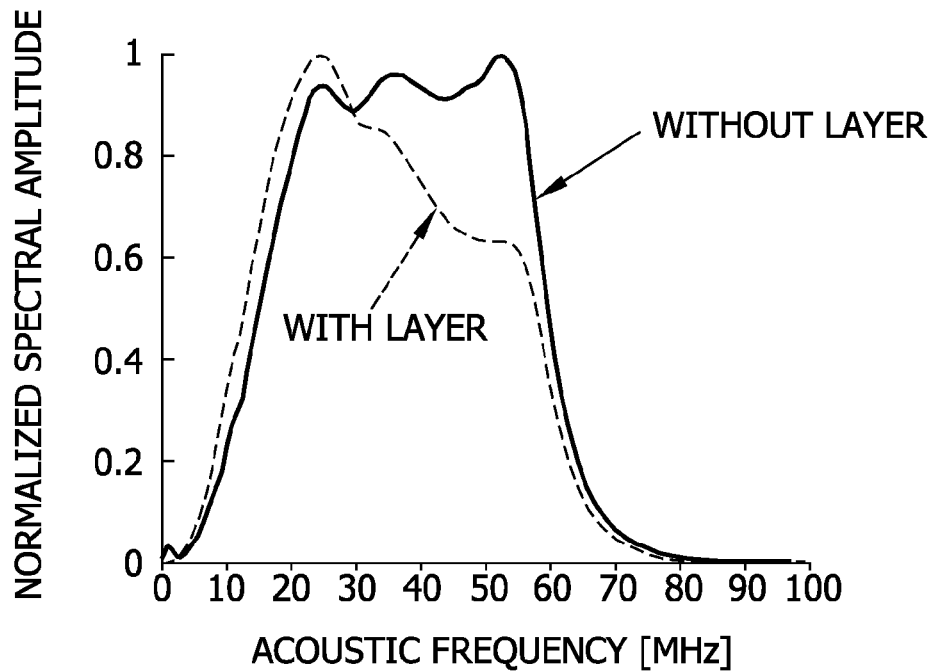
FIG. 7 is a graph illustrating acoustic spectra of a photoacoustic signal with and without an optical phantom layer.

In a phantom study, original black ink was diluted with water in six ratios ranging from 1:1 to 1:6. The original and diluted ink samples were sequentially placed in a container, sealed with plastic membrane, and then the container was placed in a water tank. Photoacoustic A-line signals were acquired from these samples. The acoustic spectra of the photoacoustic signals are shown in FIG. 4. Compared with the spectrum of the photoacoustic signal from the original ink sample, the spectra of the photoacoustic signals from the diluted ink samples are "shifted" to lower frequencies. Light penetrated deeper in lower concentration ink samples, and the corresponding photoacoustic signals decay more slowly in the time domain. Therefore, the spectra contain more low-frequency components. By dividing the measured spectra of any two ink samples frequency-by-frequency, as shown in FIG. 5, the absorption coefficients of both samples may be determined by fitting the resultant ratio curve with Eq. (3). Because parts of the spectra (e.g., 0-5 MHz and greater than 70 MHz in the exemplary system) are unreliable due to the limited-band detection, they are not used for the fitting. The quantified absorption coefficients of all seven samples and their theoretical values are plotted in FIG. 6. To demonstrate whether the recovered absorption coefficients are independent of acoustic attenuation and optical fluence, three of the ink samples were covered with an identical layer of optical phantom (~1.5 mm 2% Agar, 0.1% intralipid, 1% black ink). The spectra of the photoacoustic signals from one ink sample with and without this layer are shown in FIG. 7. The spectral profiles differ because of the acoustic attenuation, while the spectral magnitudes differ owing to the optical fluence attenuation. Since the acoustic properties of the layer added between the samples and the detector are the same for the three ink samples, the acoustic attenuation may be cancelled by taking the ratio of the acoustic spectra of photoacoustic signals from any two covered ink samples. The quantified absorption coefficients of these samples agree with the expected values as shown in FIG. 6.

Figure 8:
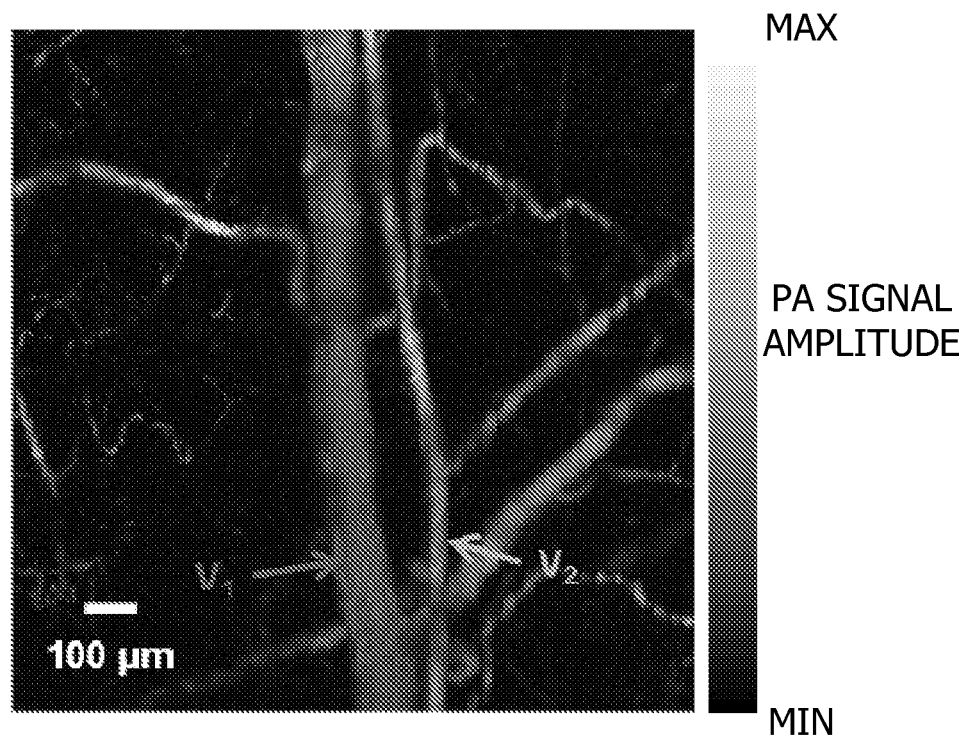
FIG. 8 is a photoacoustic maximum amplitude projection image of a blood vessel.
Figure 9:
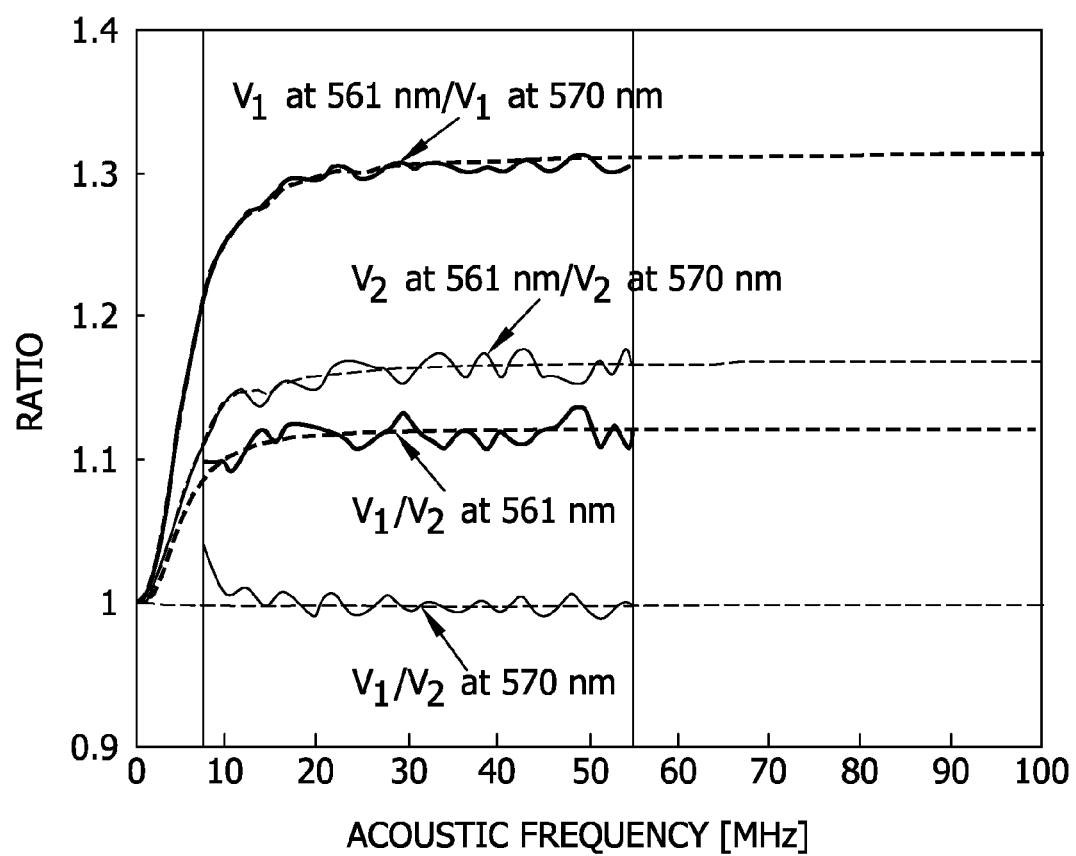
FIG. 9 is a graph that illustrates a ratio of acoustic spectra at two different optical wavelengths.

In an in vivo experiment, a region measuring approximately 1 square millimeter ($mm^2$) in a nude mouse ear was imaged with two optical wavelengths of 561 nanometers (nm) and 570 nm. FIG. 8 shows the photoacoustic maximum amplitude projection (MAP) image acquired with an optical wavelength of 570 nm, which is an oxygen insensitive absorption wavelength of hemoglobin. Each point in the MAP image records the maximum value of a Hilbert transformed photoacoustic A-scan. Two vessels marked with $V_1$ and $V_2$ in FIG. 8 were selected for a quantitative study. The A-scans acquired within these two vessels were properly aligned and then averaged. For each vessel, the acoustic spectrum measured at 561 nm was divided point by point by the acoustic spectrum measured at 570 nm, and the absorption coefficients were acquired by fitting the ratio with Eq. (3), as shown in FIG. 9. The [HbT], [HbO$_2$], and [HbR], together with the SO$_2$ values were calculated based on the quantified optical absorption coefficients at the two optical wavelengths, as shown below in Eqs. (4) and (5) and Table 1.

$$\begin{bmatrix} [HbO_2] \\ [HbR] \end{bmatrix} = \frac{64500}{2.303} \begin{bmatrix} \varepsilon_{ox}(\lambda_1) & \varepsilon_{de}(\lambda_1) \\ \varepsilon_{ox}(\lambda_2) & \varepsilon_{de}(\lambda_2) \end{bmatrix}^{-1} \begin{bmatrix} \mu_a(\lambda_1) \\ \mu_a(\lambda_2) \end{bmatrix} \quad \text{Eq. (4)}$$

$$sO_2 = \frac{[HbO_2]}{[HbO_2] + [HbR]} \quad \text{Eq. (5)}$$

Figure 13:
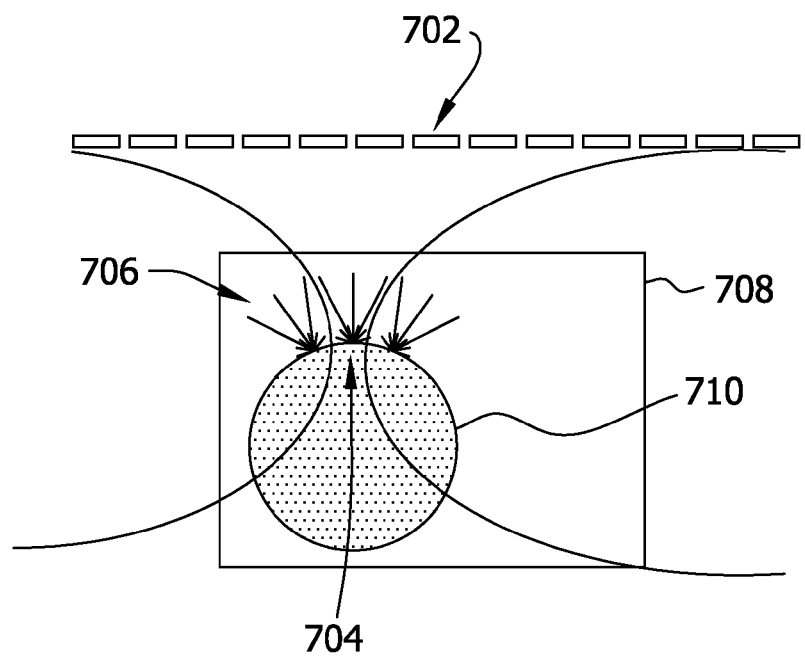
FIG. 13 is a diagram that illustrates an alternative embodiment of an OR-PAM that includes a plurality of acoustic transducers arranged into an array.

In Eq. (4), $\lambda_1$ and $\lambda_2$ are the two wavelengths, and $\varepsilon_{ox}$ and $\varepsilon_{de}$ are the known molar extinction coefficients of oxy- and deoxyhemoglobin, respectively. According to the sO$_2$ values, V$_1$ and V$_2$ were identified to be an arteriole-venule pair. The incident fluence ratio at the two optical wavelengths F($\lambda_1$)/F($\lambda_2$) was also quantified for both vessels. In this special case, the two vessels are embedded at a similar depth, and the optical and the acoustic properties of the overlying tissue are comparable. Here, the quantified fluence ratios turned out to be the same for V$_1$ and V$_2$. If the wavelength-dependent fluence variations are ignored by simply assuming F($\lambda_1$)/F($\lambda_2$)=1, as shown in the last column of Table 1, the quantified sO$_2$ values become inaccurate by approximately 8% and 11% for the artery and the vein, respectively.

each point (e.g., point 604) in a thin layer of blood 606, and the fluence F(z) in the blood vessel can be expressed as shown in Equation (6):

$$F(z) = \pi R^2 \iint_S \exp(-\mu_a \sqrt{x'^2 + y'^2 + z'^2}) dx' dy' = F_0 \pi^2 R^2 \int_0^\infty \exp(-\mu_a \sqrt{u + z^2}) du \quad \text{Eq. (6)}$$

where R is the radius of the acoustic focus 510. The object spectrum O($\omega$,$\lambda$) may then be calculated using Fourier transformation, where z is first converted to time t through z=ct. Similar to the case of OR-PAM, the system-dependent response H($\omega$) and the tissue related acoustic attenuation effect a($\omega$) are canceled by dividing, at each acoustic frequency, the acoustic spectra measured at two optical wavelengths. FIG. 13 shows another embodiment of this method with an acoustic transducer array 702. With a synthetic aperture focusing technique (SAFT), a virtual acoustic focus 704 may be formed at any position in the field of view by applying proper time delays to each element of the array system. FIG. 13 includes diffused light 706 on the surface of blood vessel 710 within tissue 708. Using the same process as described above, the optical absorption coefficients may be extracted from the acoustic spectra measured at multiple optical wavelengths. Although a linear array is illustrated in the figure, arrays of other shapes—such as a semicircle, a hemisphere, and a 2D plane—can be used as well.

To increase the accuracy of this method, an acoustic transducer with an appropriate bandwidth is selected. The acoustic spectrum of the photoacoustic signal is related to the light penetration depth. Therefore, the central frequency of the transducer should vary with the penetration depth to achieve the best signal to noise ratio (SNR). Therefore, the central

TABLE 1

| | $\mu_a(\lambda_1)$ (cm$^{-1}$) | $\mu_a(\lambda_2)$ (cm$^{-1}$) | F($\lambda_2$)/F($\lambda_1$) | [HbT] (g/L) | [HbO$_2$] (g/L) | [HbR] (g/L) | sO$_2$ | sO$_2$ F$_2$/F$_1$ = 1 |
|---|---|---|---|---|---|---|---|---|
| V$_1$ (Artery) | 143 ± 3 | 188 ± 4 | 0.96 ± 0.01 | 110.6 ± 8.1 | 106.2 ± 4.3 | 4.4 ± 3.8 | 0.96 ± 0.04 | 0.88 |
| V$_2$ (Vein) | 159 ± 4 | 186 ± 5 | 0.96 ± 0.01 | 110.2 ± 9.2 | 77.1 ± 4.9 | 33.1 ± 4.3 | 0.70 ± 0.07 | 0.62 |

Figure 10:
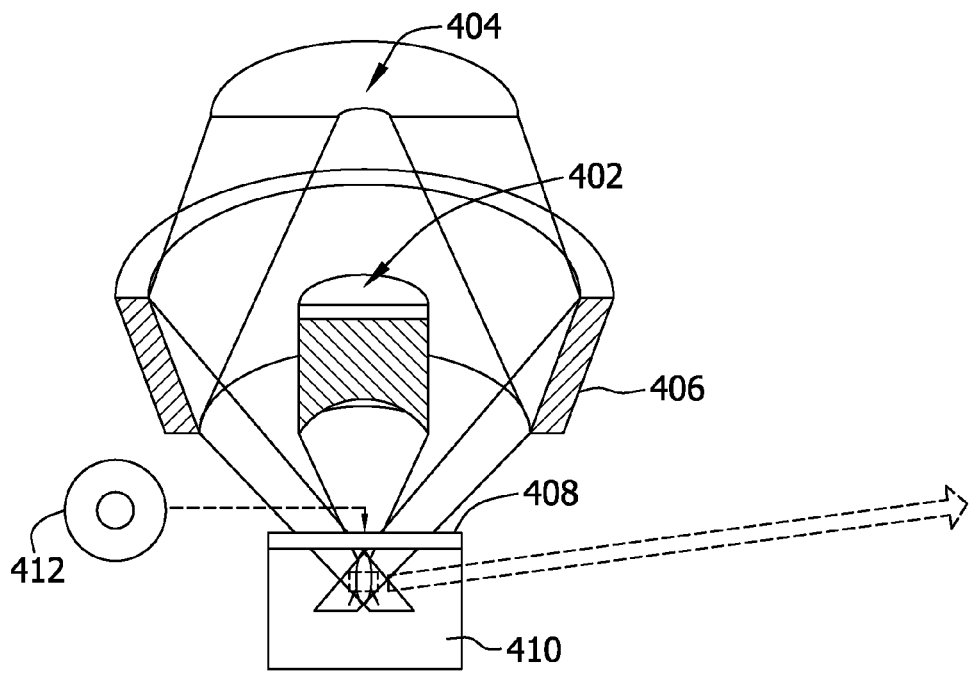
FIG. 10 is a diagram that illustrates raster scanning an acoustic transducer to obtain three-dimensional images via photoacoustic microscopy.
Figure 11:
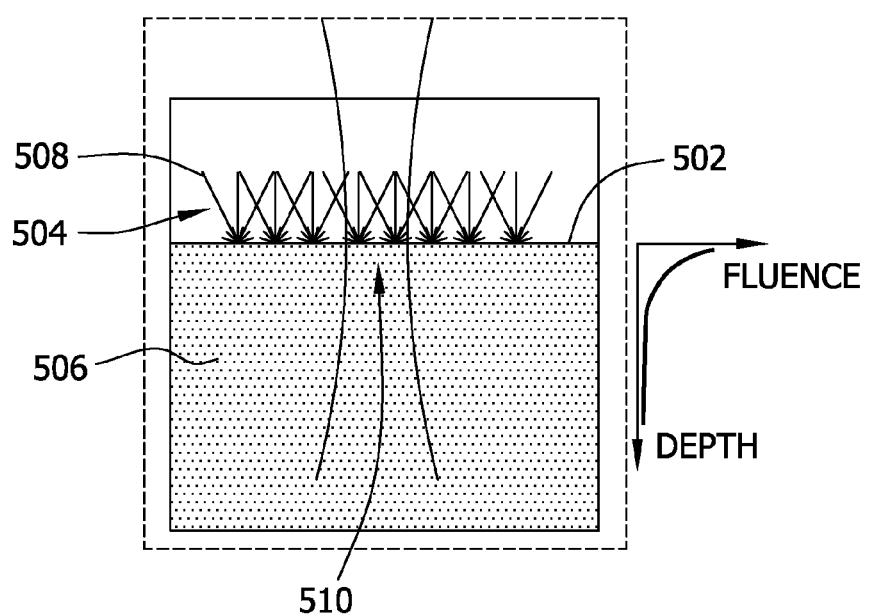
FIG. 11 is a diagram that illustrates light diffusion at or near a top surface of a blood vessel.
Figure 12:
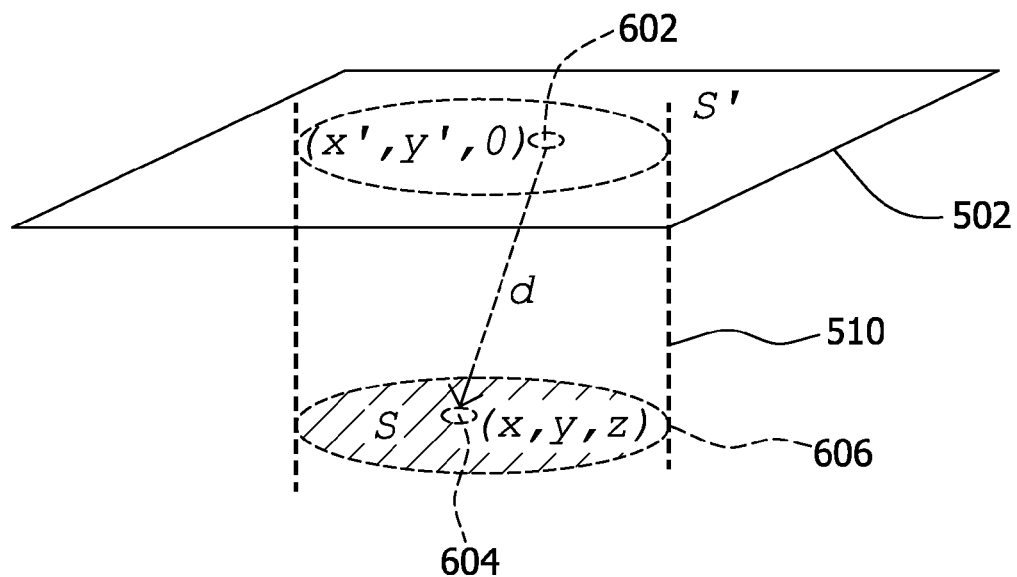
FIG. 12 is a diagram that illustrates a characterization of light on the top surface of the blood vessel of FIG. 11 as an isotropic point source.

Embodiments of the method may be applied in the optical diffusive regime with photoacoustic microscopy, whose lateral resolution relies on the acoustic focus (e.g., ~50 µm at 50 MHz acoustic frequency). As shown in FIG. 10, photoacoustic A-scan signals are acquired through time-resolved acoustic detection, and three-dimensional images are formed by raster scanning an acoustic transducer 402 and optical components (e.g., optical illumination source 404 and mirror 406) along a transverse plane (e.g., transverse to the direction of the optical illumination striking a surface 408 of a sample 410). In the embodiment of FIG. 10, the surface 408 of the sample 410 is illuminated with an annular ring having a dark center 412 as shown in the call out from the main figure. The surface of blood vessels with sufficiently large diameter (e.g., greater than 300 µm for the 50-µm lateral resolution) may be approximately treated as a flat surface. As shown in FIG. 11, it may generally be assumed that the light is completely diffused (e.g., see diffused light 504) when it reaches a top surface 502 of a blood vessel within tissue 410. Blood 506 is located below the blood vessel top surface 502, overlying tissue 508 is located above the blood vessel top surface 502, and the acoustic focus 510 narrows at the surface of the blood vessel 502 as shown in FIG. 11. Moreover, as shown in FIG. 12, light at each point (e.g., point 602) on the top surface of the blood vessel 502 can be seen as an isotropic point source for frequency of the transducer should match the penetration depth to maximize signal to noise ratio (SNR). Moreover, SNR is usually low at high acoustic frequencies due to acoustic attenuation. O($\omega$,$\lambda$), H($\omega$), and a($\omega$) are all band-limited, and in an exemplary embodiment, H($\omega$) is chosen to match O($\omega$,$\lambda$) and a($\omega$).

Figure 14:
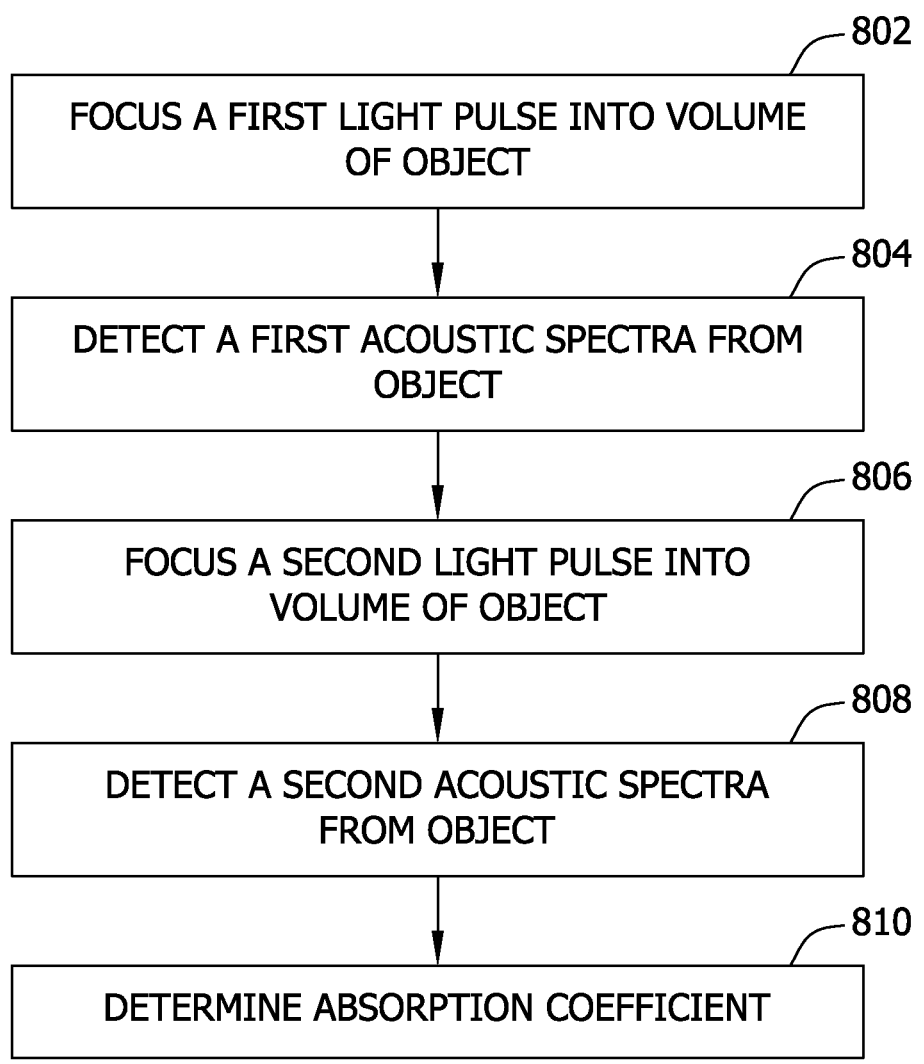
FIG. 14 is a flow chart of a method of determining an absorption coefficient of a volume of an object.

Referring to FIG. 14, a method of determining an absorption coefficient of a volume of an object begins with a focusing element (e.g., an objective or lens) focuses a first light pulse from a light source (e.g., a laser) into a volume of an object or sample at 802. At 804, a transducer detects a first acoustic spectrum emitted by the object in response to the volume of the object receiving the first light pulse. At 806, the focusing element focuses a second light pulse from the light source into the volume of the object, and at 808, the transducer detects a second acoustic spectrum emitted by the object in response to the volume of the object receiving the second light pulse. In operation, the transducer receives an acoustic wave from the object and performs a Fourier transform to generate the acoustic spectrum. It is contemplated that the Fourier transform may be performed by a component separate from the transducer component receiving the acoustic waveform. At 810, a controller determines an absorption coefficient from the detected first and second acoustic spectra by dividing the first acoustic spectrum by the second acoustic spectrum frequency by frequency yielding a normalized acoustic spectrum. The normalized acoustic spectrum is fitted to an ideal curve of an absorption coefficient to determine the absorption coefficient of the volume of the object. The first and second light pulses have different wavelengths, and the method may be repeated for multiple volumes of the object and to obtain an image of the object.

It will be understood that the particular embodiments described herein are shown by way of illustration and not as limitations of the disclosure. The principal features of this disclosure may be employed in various embodiments without departing from the scope of the disclosure. Those of ordinary skill in the art will recognize numerous equivalents to the specific procedures described herein. Such equivalents are considered to be within the scope of this disclosure and are covered by the claims.

All of the compositions and/or methods disclosed and claimed herein may be made and/or executed without undue experimentation in light of the present disclosure. While the compositions and methods of this disclosure have been described in terms of the embodiments included herein, it will be apparent to those of ordinary skill in the art that variations may be applied to the compositions and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although preferred embodiments of the present disclosure have been described in detail, it will be understood by those skilled in the art that various modifications can be made therein without departing from the spirit and scope of the disclosure as set forth in the appended claims.

A controller, computing device, or computer, such as described herein, includes at least one or more processors or processing units and a system memory. The controller typically also includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of quantifying an absolute optical absorption coefficient of an object, said method comprising:
   focusing a first light pulse emitted by a light source into a volume of the object, wherein the first light pulse has a first wavelength;
   receiving at an acoustic transducer a first acoustic wave emitted by the object in response to receiving the first light pulse;
   performing on a controller a transformation on the received first acoustic wave to generate a first acoustic spectrum;
   focusing a second light pulse emitted by the light source into the volume of the object, wherein the second light pulse has a second wavelength;
   receiving at the acoustic transducer a second acoustic wave emitted by the object in response to receiving the second light pulse;
   performing on the controller a transformation on the received second acoustic wave to generate a second acoustic spectrum; and
   quantifying the absolute absorption coefficient of the volume of the object, wherein the absolute absorption coefficient is a function of the first acoustic spectrum and the second acoustic spectrum.

2. The method of claim 1 wherein the transformation performed on the received first acoustic wave to generate the first acoustic spectrum comprises a Fourier transformation.

3. The method of claim 1 wherein the transformation performed on the received second acoustic wave to generate the second acoustic spectrum comprises a Fourier transformation.

4. The method of claim 1 wherein quantifying the absolute absorption coefficient of the volume of the object comprises dividing the first acoustic spectrum by the second acoustic spectrum frequency by frequency to generate a normalized acoustic spectrum, and fitting the normalized acoustic spectrum to an absorption coefficient curve.

5. The method of claim 1 wherein the light source comprises a first light source for emitting the first light pulse and a second light source for emitting the second light pulse.

6. The method of claim 1 wherein the first wavelength is different from the second wavelength.

7. The method of claim 1 further comprising disregarding a portion of the first acoustic spectrum and the second acoustic spectrum outside of a system bandwidth, wherein the system bandwidth is at least partially determined as a function of a bandwidth of the acoustic transducer.

8. The method of claim 1 further comprising determining at least one of absolute HbT, absolute $HbO_2$, absolute HbR, and $sO_2$ values as a function of the quantified absolute absorption coefficient.

9. A system for quantifying an absolute optical absorption coefficient of a volume of an object, said system comprising:
a light source for emitting a first light pulse having a first wavelength and a second light pulse having a second wavelength;
a focusing element for focusing the first light pulse and the second light pulse into a volume of the object;
an acoustic transducer for receiving a first acoustic wave emitted by the object in response to the volume of the object absorbing the first light pulse and a second acoustic wave emitted by the object in response to the volume of the object absorbing the second light pulse; and
a controller for performing a transformation on the received first acoustic wave and second acoustic wave to generate a first acoustic spectrum and a second acoustic spectrum, respectively, and quantifying the absolute absorption coefficient of the volume of the object as a function of the first acoustic spectrum and the second acoustic spectrum.

10. The system of claim 9 wherein:
the transformation performed by the controller on the received first acoustic wave to generate the first acoustic spectrum is a Fourier transformation; and
the transformation performed by the controller on the received second acoustic wave to generate the second acoustic spectrum is a Fourier transformation.

11. The system of claim 9 wherein the controller is further configured to quantify the absolute absorption coefficient of the volume of the object by dividing the first acoustic spectrum by the second acoustic spectrum, frequency by frequency, to generate a normalized acoustic spectrum and to fit the normalized acoustic spectrum to an absorption coefficient curve.

12. The system of claim 9 wherein the light source comprises a first light source for emitting the first light pulse and a second light source for emitting the second light pulse, and wherein the first wavelength is different from the second wavelength.

13. The system of claim 9 wherein the controller is further configured to disregard a portion of the first acoustic spectrum and the second acoustic spectrum outside of a system bandwidth, wherein said system bandwidth is at least partially determined as a function of a bandwidth of the acoustic transducer.

14. The system of claim 9 wherein the controller is configured to quantify at least one of absolute HbT, absolute $HbO_2$, absolute HbR, and $sO_2$ values as a function of the quantified absolute absorption coefficient.

15. A system for generating an image of an object and quantifying an absolute optical absorption coefficient of a volume of an object, said system comprising:
a light source for emitting a first light pulse having a first wavelength and a second light pulse having a second wavelength;
a focusing element for focusing the first light pulse and the second light pulse into a volume of a plurality of volumes of the object;
an acoustic transducer for receiving a first acoustic wave produced by the object in response to the volume of the object absorbing the first light pulse and a second acoustic wave produced by the object in response to the volume of the object absorbing the second light pulse;
a controller for performing a transformation on the received first acoustic wave and second acoustic wave to generate a first acoustic spectrum and a second acoustic spectrum, respectively, quantifying the absolute absorption coefficient of the volume of the object as a function of the first acoustic spectrum and the second acoustic spectrum and for reconstructing an image from acoustic spectra detected from the plurality of volumes of the object; and
a scanner for altering a spatial relationship between the object and the focusing element after the first acoustic wave and the second acoustic wave are detected by the acoustic transducer for the volume such that the first light pulse and the second light pulse are focused into another volume of the plurality of volumes of the object.

16. The system of claim 15 wherein:
the transformation performed by the controller on the received first acoustic wave to generate the first acoustic spectrum is a Fourier transformation; and
the transformation performed by the controller on the received second acoustic wave to generate the second acoustic spectrum is a Fourier transformation.

17. The system of claim 15 wherein the controller is configured to quantify the absolute absorption coefficient of the volume of the object by dividing the first acoustic spectrum by the second acoustic spectrum, frequency by frequency, to generate a normalized acoustic spectrum and fits the normalized acoustic spectrum to an absorption coefficient curve.

18. The system of claim 15 wherein the light source comprises a first light source for emitting the first light pulse and a second light source for emitting the second light pulse, and wherein the first wavelength is different from the second wavelength.

19. The system of claim 15 wherein the controller is configured to disregard a portion of the first acoustic spectrum and the second acoustic spectrum outside of a system bandwidth, wherein said system bandwidth is at least partially determined as a function of a bandwidth of the transducer.

20. The system of claim 15 wherein the controller is configured to quantify at least one of absolute HbT, absolute $HbO_2$, absolute HbR, and $sO_2$ values as a function of the quantified absolute absorption coefficient.

* * * * *